US012721645B2

(12) United States Patent
Van Liere

(10) Patent No.: US 12,721,645 B2
(45) Date of Patent: Sep. 1, 2026

(54) ATHERECTOMY CATHETER AND SYSTEM

(71) Applicant: Bard Peripheral Vascular, Inc., Franklin Lakes, NJ (US)

(72) Inventor: Chad Van Liere, Phoenix, AZ (US)

(73) Assignee: Bard Peripheral Vascular, Inc., Franklin Lakes, NJ (US)

(*) Notice: Subject to any disclaimer, the term of this patent is extended or adjusted under 35 U.S.C. 154(b) by 710 days.

(21) Appl. No.: 18/002,712

(22) PCT Filed: Jun. 26, 2020

(86) PCT No.: PCT/US2020/039775
§ 371 (c)(1),
(2) Date: Dec. 21, 2022

(87) PCT Pub. No.: WO2021/262189
PCT Pub. Date: Dec. 30, 2021

(65) Prior Publication Data

US 2023/0240710 A1 Aug. 3, 2023

(51) Int. Cl.
*A61B 17/3207* (2006.01)
*A61B 17/00* (2006.01)
*A61B 17/32* (2006.01)

(52) U.S. Cl.
CPC ................. *A61B 17/320783* (2013.01); *A61B 2017/00477* (2013.01); *A61B 2017/00871* (2013.01);
(Continued)

(58) Field of Classification Search
CPC .. A61B 17/320783; A61B 2017/00477; A61B 2017/00871; A61B 2017/320069; A61B 2017/320084; A61B 2017/320098; A61B 2017/320791; A61B 2017/22015; A61B 2017/22094; A61B 2090/034; A61B 17/22012; A61B 17/320758;
(Continued)

(56) References Cited

U.S. PATENT DOCUMENTS 4,178,935 A * 12/1979 Gekhman .......... A61B 17/3207 606/128
5,234,451 A 8/1993 Osypka
5,554,163 A * 9/1996 Shturman ...... A61B 17/320783 606/159
5,702,413 A * 12/1997 Lafontaine ........ A61M 25/0043 606/191

(Continued)

FOREIGN PATENT DOCUMENTS

DE 4036570 A1 5/1992

OTHER PUBLICATIONS

International Search Report and Written Opinion dated Mar. 19, 2021, in International Application No. PCT/US2020/039775.

*Primary Examiner* — Tan-Uyen T Ho
*Assistant Examiner* — Bridget E. Rabaglia
(74) *Attorney, Agent, or Firm* — Dinsmore & Shohl LLP

(57) ABSTRACT

An atherectomy catheter includes a sheath and an elongate corewire. The sheath has a side wall configured to define, in a lumen and in a distal sheath portion, an entrapment boundary region having a drilling allowance region. The elongate corewire has a distal wire portion having an outer bulge portion that is proximal to an elongate drill tip portion. The elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath.

20 Claims, 3 Drawing Sheets

(52) U.S. Cl.
CPC ............. *A61B 2017/320069* (2017.08); *A61B 2017/320084* (2013.01); *A61B 2017/320098* (2017.08); *A61B 2017/320791* (2013.01)

(58) Field of Classification Search
CPC .. A61B 17/320725; A61B 2017/22038; A61B 2017/320004; A61B 17/3207; A61B 17/22; A61B 2017/320766; A61B 8/12; A61B 18/1492; A61B 2017/320775; A61B 2017/22067; A61B 18/245; A61B 2217/007; A61B 17/32002; A61B 2017/22072; A61B 2017/22074; A61B 2017/22075; A61B 2017/22077; A61B 2017/22078; A61B 2017/22042; A61B 2017/22044; A61B 2017/22045; A61B 2017/22047; A61B 17/22004; A61B 2017/22027; A61B 17/2202
See application file for complete search history.

(56) References Cited

U.S. PATENT DOCUMENTS

| | | | |
|---|---|---|---|
| 8,167,821 | B2 | 5/2012 | Sharrow |
| 8,556,926 | B2 | 10/2013 | Duerig et al. |
| 9,060,806 | B2 | 6/2015 | Thatipelli |
| 9,095,370 | B2 | 8/2015 | Wilkinson |
| 9,119,651 | B2 | 9/2015 | Katoh et al. |
| 9,387,308 | B2 | 7/2016 | Jinchliffe et al. |
| 10,195,401 | B2 | 2/2019 | Hansen et al. |
| 10,285,710 | B2 | 5/2019 | Lorenzo et al. |
| 10,463,386 | B2 | 11/2019 | Ogle et al. |
| 10,518,066 | B2 | 12/2019 | Pokorney et al. |
| 2005/0059981 | A1 | 3/2005 | Poll |
| 2018/0207407 | A1 | 7/2018 | Tanigaki |
| 2020/0054864 | A1 | 2/2020 | Vrancken Peeters et al. |
| 2020/0094027 | A1 | 3/2020 | Davis |

* cited by examiner

ATHERECTOMY CATHETER AND SYSTEM

CROSS-REFERENCE TO RELATED APPLICATIONS

This application is a U.S. National Phase of International Application No. PCT/US2020/039775, entitled "Atherectomy Catheter and System" and filed Jun. 26, 2020, which is incorporated herein by reference in its entirety.

TECHNICAL FIELD

The present invention relates to an ultrasonic system, and more particularly, to an atherectomy catheter and system for performing an atherectomy procedure.

BACKGROUND ART

Surgical procedures, such as a crossing procedure or an atherectomy procedure, may be used to restore patency and blood flow that was lost due to one or more intravascular occlusions. A crossing procedure is a procedure in which an opening is formed through the intravascular occlusion. An atherectomy procedure may include crossing, but also attempts to break up and remove the intravascular lesion that forms an occlusion in the blood vessel. An ultrasonic system having an ultrasonic catheter may be used in performing crossing and atherectomy procedures.

One type of procedure includes directly engaging the intravascular lesion with an exposed instrument, such as a stiff yet flexible elongate wire. However, there is a possibility of wire breakage, such as for example, when the wire is energized with ultrasonic vibration and the wire is intermittently engaged with the intravascular lesion.

What is needed in the art is an atherectomy catheter having features that retain a distal wire portion of a corewire of the atherectomy catheter in the event of corewire breakage.

SUMMARY OF INVENTION

The present invention provides an atherectomy catheter having features that retain a distal wire portion of a corewire of the atherectomy catheter in the event of corewire breakage.

The invention, in one form, is directed to an atherectomy catheter that includes a sheath and an elongate corewire. The sheath has a side wall configured to define a lumen. The sheath has a distal sheath portion and a distal end. The side wall is configured to define in the lumen an entrapment boundary region in the distal sheath portion. The entrapment boundary region has a drilling allowance region. The elongate corewire has a proximal wire portion and a distal wire portion. The distal wire portion has an outer bulge portion and an elongate drill tip portion. The outer bulge portion is proximal to the elongate drill tip portion. The elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath.

The invention, in another form, is directed to an atherectomy system that includes an ultrasonic energy source and an atherectomy catheter. The ultrasonic energy source is configured to operate in a drilling mode and a radial ablation mode. The atherectomy catheter is coupled, or configured for coupling, to the ultrasonic energy source. The ultrasonic energy source is configured to effect a longitudinal motion of the atherectomy catheter in the drilling mode and to effect both longitudinal motion and transverse motion of the atherectomy catheter in the radial ablation mode. The atherectomy catheter includes a sheath and an elongate corewire. The sheath has a side wall configured to define a lumen. The sheath has a distal sheath portion and a distal end. The side wall is configured to define in the lumen an entrapment boundary region in the distal sheath portion. The entrapment boundary region has a drilling allowance region. An elongate corewire has a proximal wire portion and a distal wire portion. The distal wire portion has an outer bulge portion and an elongate drill tip portion. The outer bulge portion is proximal to the elongate drill tip portion. The elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath.

An advantage of the present invention is that the entrapment boundary region in the distal sheath portion of the atherectomy catheter is configured to retain the distal wire portion of the atherectomy catheter in the event of corewire breakage.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
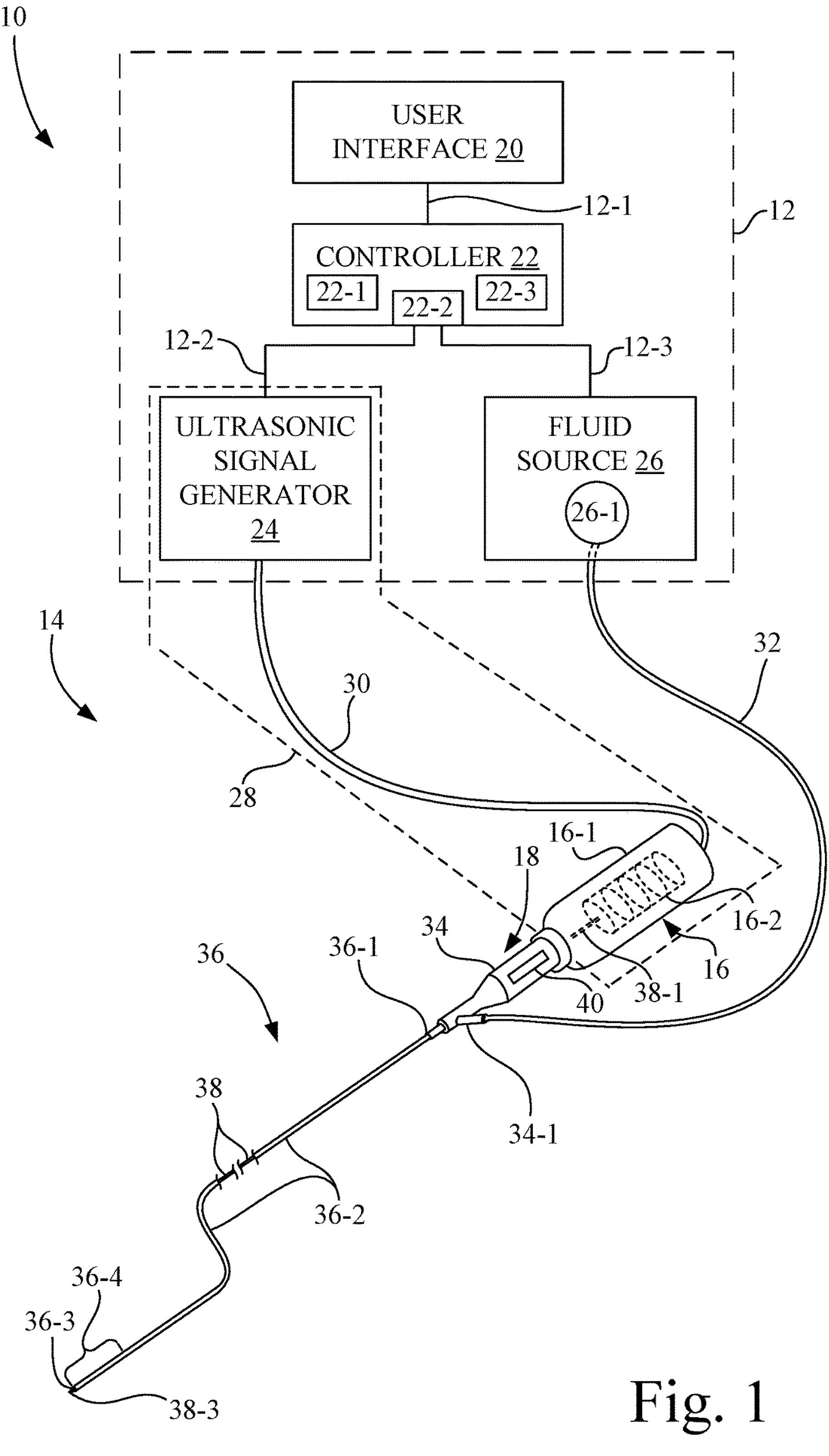
FIG. 1 is a schematic illustration of an atherectomy system in accordance with an embodiment of the present invention, which includes a console, and an ultrasonic device that includes an atherectomy catheter having a sheath and an elongate corewire.

Referring now to the drawings, and more particularly to FIG. 1, there is shown an atherectomy system 10 in accordance with an embodiment of the present invention. In the present embodiment, atherectomy system 10 includes a console 12 and an ultrasonic device 14.

Ultrasonic device 14 may be used, for example, for interventional vascular occlusion procedures. Ultrasonic device 14 includes a handpiece 16 and an atherectomy catheter 18. Handpiece 16 includes a housing body 16-1 and an ultrasonic transducer 16-2 mounted internally to housing body 16-1. Housing body 16-1 has an outer shape and size to facilitate being grasped by a user, e.g., a physician, during an atherectomy procedure. Console 12 may include, for example, a user interface 20, a controller 22, an ultrasonic signal generator 24, and a fluid source 26. In combination, ultrasonic signal generator 24 of console 12 and ultrasonic transducer 16-2 of ultrasonic device 14 form an ultrasonic energy source 28 that is operatively coupled to atherectomy catheter 18. Ultrasonic energy source 28 is configured to operate in a drilling (crossing) mode and a radial ablation (atherectomy) mode, wherein ultrasonic energy source 28 is configured to effect a longitudinal motion of atherectomy catheter 18 in the drilling mode, and is configured to effect both longitudinal motion and transverse motion of atherectomy catheter 18 in the radial ablation mode.

Ultrasonic transducer 16-2 of ultrasonic device 14 may be, for example, a piezoelectric-type transducer. Ultrasonic transducer 16-2 of handpiece 16 is electrically connected to ultrasonic signal generator 24 by an electrical cable 30. Ultrasonic transducer 16-2 is configured to receive and convert an ultrasonic excitation signal (electrical) generated by ultrasonic signal generator 24 into ultrasonic vibrational energy.

User interface 20 of console 12 is connected to controller 22 via an electrical conductor 12-1, e.g., a multi-wire cable or USB, to provide electrical and communication interconnection. Alternatively, user interface 20 may be a wireless link, e.g., Bluetooth, which is communicatively coupled to controller 22. User interface 20 may include, for example, a touchscreen display and associated input and output processing circuitry. Touchscreen display may include, for example, a liquid crystal display (LCD) or a light-emitting diode (LED) display. Alternatively, user interface 20 may be in the form of a laptop computer or tablet. User interface 20 is configured to generate control signals based on user input. For example, a user may operate user interface 20 to provide the control signals to controller 22 to initiate, control, and/or terminate operation of ultrasonic signal generator 24, and/or to selectively start, stop, or control the fluid feed rate of fluid source 26.

Controller 22 is electrically connected and communicatively coupled to user interface 20 via electrical conductor 12-1, e.g., a multi-wire cable or USB. Also, controller 22 is electrically connected and communicatively coupled to ultrasonic signal generator 24 via an electrical conductor 12-2, e.g., a multi-wire cable or USB, and controller 22 is electrically connected and communicatively coupled to fluid source 26 via an electrical conductor 12-3, e.g., a multi-wire cable or USB. Each of electrical conductors 12-2, 12-3 is configured to carry respective output control signals.

Controller 22 includes a processor circuit 22-1, interface circuitry 22-2, and an electronic memory circuit 22-3. Controller 22 executes program instructions to process signals received from user interface 20, executes program instructions to provide output control signals via interface circuit 22-2 to ultrasonic signal generator 24 to control the operation of ultrasonic signal generator 24, and executes program instructions to provide output control signals via interface circuit 22-2 to fluid source 26 to control the operation of fluid source 26.

Processor circuit 22-1 of controller 22 may include one or more programmable microprocessors and associated circuitry, such as an input/output interface, clock, buffers, memory, etc. Processor circuit 22-1 may be programmed, e.g., through software or firmware stored in electronic memory circuit 22-3, to execute program instructions to process received input data, and to generate and send output data to ultrasonic signal generator 24 and/or fluid source 26.

Interface circuitry 22-2 includes input and output circuits to facilitate electrical connection and data transfer with user interface 20, ultrasonic signal generator 24, and fluid source 26.

Electronic memory circuit 22-3 is an electronic non-transitory memory having a plurality of data storage locations, as is well known in the art. Electronic memory circuit 22-3 may be used, for example, to store program instructions to be executed by processor circuit 22-1 of controller 22 of console 12.

Ultrasonic signal generator 24 is typical of that known in the art, and may be controlled via user interface 20 and controller 22 to produce an ultrasonic electrical signal in the form of an ultrasonic excitation signal, e.g., in a frequency range of 20 kHz-40 kHz, that is supplied to ultrasonic transducer 16-2. Ultrasonic transducer 16-2 is configured to receive and convert the ultrasonic excitation signal generated by ultrasonic signal generator 24 into ultrasonic vibrational energy, which may be in a frequency range corresponding to that of the ultrasonic excitation signal.

Fluid source 26 may be, for example, a saline injector, and includes a pump 26-1 that is configured to supply a heat dissipating fluid, e.g., sterile saline, to ultrasonic device 14. A secondary use of heat dissipating fluid may be to flush a procedure area in the patient during a medical procedure.

Atherectomy catheter 18 includes a housing 34, a sheath 36, and an elongate corewire 38. Housing 34 includes a Y-connector 34-1 that provides access to an irrigation lumen of sheath 36. Y-connector 34-1 is connected, e.g., by a flexible hose 32, to fluid source 26. In the present embodiment, housing 34 further includes a retraction-extension mechanism 40, such as a slide, that is connected to sheath 36.

Figures 2, 3:
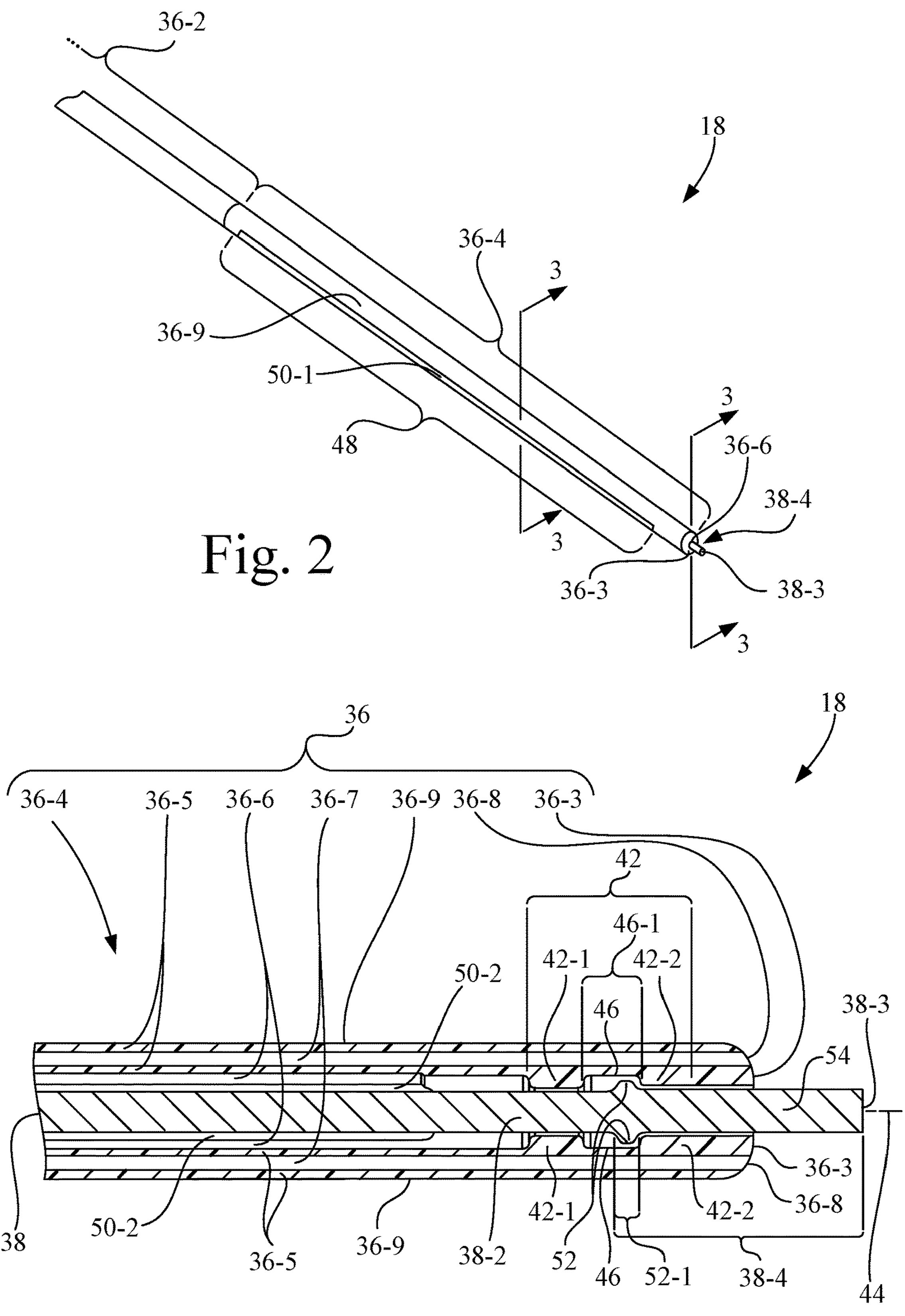
FIG. 2 is a perspective view of a broken away portion of the atherectomy catheter of FIG. 1 that shows a portion of the proximal sheath portion and the full distal sheath portion of the sheath, and a portion of a corewire, of the atherectomy catheter.
FIG. 3 is an enlarged section view of a portion of the broken away portion of the atherectomy catheter of FIG. 2, taken along plane 3-3-3-3 of FIG. 2.

Referring to FIGS. 1-3, sheath 36 is an elongate flexible tube, such as a flexible biocompatible polymer tube. Sheath 36 includes a proximal end 36-1, a proximal sheath portion 36-2, a distal end 36-3, a distal sheath portion 36-4, and a side wall 36-5 configured to define a corewire lumen 36-6 and at least one elongate fluid passage 36-7. Each elongate fluid passage 36-7 is in fluid communication with Y-connector 34-1 of atherectomy catheter 18. Sheath 36 may have a length greater than 60 centimeters (cm), and in some embodiments, a length of 100 to 200 cm. In the present embodiment, corewire lumen 36-6 is an elongate lumen that longitudinally extends within sheath 36 from proximal end 36-1 to distal end 36-3, and may be formed as a central lumen, relative to the diameter, of sheath 36. Proximal end 36-1 of sheath 36 of atherectomy catheter 18 is connected to housing 34 of atherectomy catheter 18, and optionally may be connected to a retraction-extension mechanism 40, e.g., a slider button to facilitate the retraction and extension of sheath 36 relative to housing 34 of atherectomy catheter 18. The at least one elongate fluid passage 36-7 is formed in side wall 36-5 of sheath 36, wherein each elongate fluid passage 36-7 has a distal fluid port 36-8 located at distal end 36-3 of sheath 36.

Side wall 36-5 is configured to define in corewire lumen 36-6 an entrapment boundary region 42 in distal sheath portion 36-4. Entrapment boundary region 42 has a proximal interior protrusion 42-1 and a distal interior protrusion 42-2. Proximal interior protrusion 42-1 and distal interior protrusion 42-2 are axially spaced apart along a longitudinal axis 44 to define a drilling allowance region 46 between proximal interior protrusion 42-1 and distal interior protrusion 42-2. Proximal interior protrusion 42-1 of sheath 36 may be configured, for example, as a proximal interior annular member. Likewise, distal interior protrusion 42-2 of sheath 36 may be configured, for example, as a distal interior annular member.

Side wall 36-5 of sheath 36 may include one or more elongate fluid passages 36-7, e.g., formed in side wall 36-5, wherein each elongate fluid passage 36-7 longitudinally extends along entrapment boundary region 42 to provide cooling to distal wire portion 38-4 of elongate corewire 38.

Referring to FIGS. 2-5, side wall 36-5 of sheath 36 includes a slotted region 48 in distal sheath portion 36-4, wherein slotted region 48 is proximal to entrapment boundary region 42. In the present embodiment, slotted region 48 has a pair of diametrically opposed elongate slots that are individually identified as elongate slot 50-1 and elongate slot 50-2, wherein each of elongate slot 50-1 and elongate slot 50-2 radially extends through side wall 36-5 of sheath 36 from an outer surface 36-9 of side wall 36-5 to corewire lumen 36-6.

Elongate corewire 38 is made of a biocompatible metal e.g., nitinol, and is in the form of an elongate flexible biocompatible metal wire. Elongate corewire 38 is located in, and longitudinally extends within, corewire lumen 36-6 of sheath 36. Elongate corewire 38 has a proximal end 38-1, a proximal wire portion 38-2, a distal tip 38-3, and a distal wire portion 38-4. Proximal end 38-1 of elongate corewire 38 is operably connected to ultrasonic transducer 16-2, e.g., by a sonic connector, to receive the ultrasonic vibrational energy from ultrasonic transducer 16-2 so as to produce ultrasonic vibrational motion of elongate corewire 38. As such, elongate corewire 38 may sometimes be referred to in the art as an ultrasonic transmission member.

For example, with reference to FIGS. 1 and 2, ultrasonic energy source 28 is configured to effect a longitudinal motion of elongate corewire 38 of atherectomy catheter 18 in the drilling (crossing) mode, and is configured to effect both longitudinal motion and transverse motion of elongate corewire 38 of atherectomy catheter 18 in the radial ablation (atherectomy) mode. In the drilling mode, for example, the user may operate controller 22 to execute program instructions to select a predetermined energy level output and a predominately sinusoidal waveform for the ultrasonic excitation signal generated by ultrasonic signal generator 24 that is supplied to ultrasonic transducer 16-2, so as to effect primarily longitudinal vibrational motion of elongate corewire 38. In the radial ablation mode, for example, the user may operate controller 22 to execute program instructions to select a higher predetermined energy level output and/or select a complex (e.g., multiple combined sinusoids) waveform for the ultrasonic excitation signal generated by ultrasonic signal generator 24 that is supplied to ultrasonic transducer 16-2, so as to effect a combination of longitudinal and transverse vibrational motion of elongate corewire 38. In other words, the vibrational motion of elongate corewire 38 may be predominantly (if not exclusively) longitudinal motion in the drilling mode, or may be a combination of longitudinal and transverse vibrational motion in the radial ablation mode.

Distal wire portion 38-4 of elongate corewire 38 has an outer bulge portion 52 and an elongate drill tip portion 54. Outer bulge portion 52 is proximal to elongate drill tip portion 54. Stated differently, elongate drill tip portion 54 extends distally from outer bulge portion 52.

Elongate corewire 38 is located in corewire lumen 36-6 of sheath 36, wherein outer bulge portion 52 of elongate corewire 38 is received in a snap-fit in drilling allowance region 46 of sheath 36 between proximal interior protrusion 42-1 and distal interior protrusion 42-2 of sheath 36. In other words, during assembly, corewire 38 is move distally into contact with proximal interior protrusion 42-1, and proximal interior protrusion 42-1 radially deflects so that outer bulge portion 52 of elongate corewire 38 may be received in drilling allowance region 46 of sheath 36 between proximal interior protrusion 42-1 and distal interior protrusion 42-2 of sheath 36. Thus, once assembled, outer bulge portion 52 of elongate corewire 38 is slidably disposed in drilling allowance region 46 of sheath 36 between proximal interior protrusion 42-1 and distal interior protrusion 42-2 of sheath 36, and with elongate drill tip portion 54 of elongate corewire 38 distally protruding from distal end 36-3 of sheath 36. Outer bulge portion 52 of elongate corewire 38 may be configured, for example, as an outer (e.g., outwardly radially extending) annular member.

Drilling allowance region 46 of sheath 36 has a longitudinal extent 46-1 and outer bulge portion 52 of elongate corewire 38 has a longitudinal width 52-1, wherein the longitudinal extent 46-1 of drilling allowance region 46 of sheath 36 is greater than the longitudinal width 52-1 of outer bulge portion 52 of elongate corewire 38 so as to accommodate alternating proximal and distal movement (i.e., longitudinal reciprocating movement) of distal wire portion 38-4 of elongate corewire 38. Stated differently, proximal interior protrusion 42-1 of sheath 36 defines a proximal limit of longitudinal movement of distal tip 38-3 of elongate drill tip portion 54 of elongate corewire 38, and distal interior protrusion 42-2 of sheath 36 defines a distal limit of longitudinal movement of distal tip 38-3 of elongate drill tip portion 54 of elongate corewire 38. In the drilling mode, for example, distal tip 38-3 of elongate drill tip portion 54 of elongate corewire 38, which extends distally from distal end 36-3 of sheath 36, may be longitudinally reciprocated to engage and anchor into the cap of the lesion forming an occlusion in a blood vessel.

Entrapment boundary region 42 of sheath 36 and outer bulge portion 52 of elongate corewire 38 are configured so as to retain distal wire portion 38-4 with sheath 36 in the event that proximal wire portion 38-2 of elongate corewire 38 separates, e.g., breaks, from distal wire portion 38-4 of elongate corewire 38. Stated differently, entrapment boundary region 42 of sheath 36 and outer bulge portion 52 of elongate corewire 38 are configured to help prevent distal wire portion 38-4 of elongate corewire 38 from being separated from sheath 36, e.g., and temporarily lost into the blood vessel, in the event that distal wire portion 38-4 of elongate corewire 38 separates, e.g., breaks, from proximal wire portion 38-2 of elongate corewire 38 during an atherectomy procedure.

Figure 4:
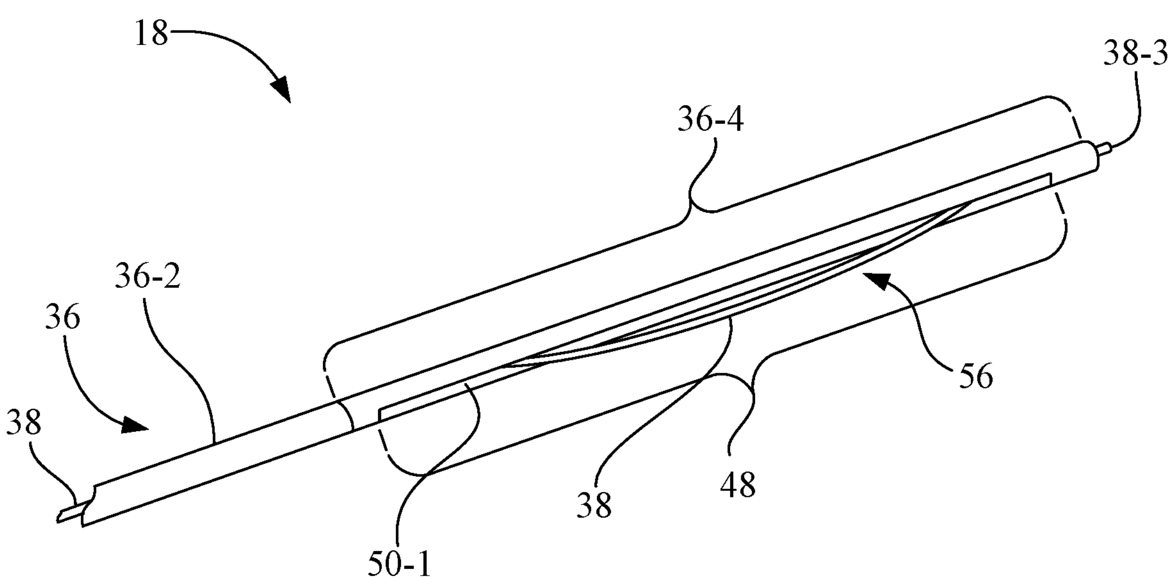
FIG. 4 is a perspective view of a broken away portion of the atherectomy catheter of FIG. 1 that shows a bend portion of the elongate corewire radially extending through a first elongate slot of the sheath of the atherectomy catheter.
Figure 5:
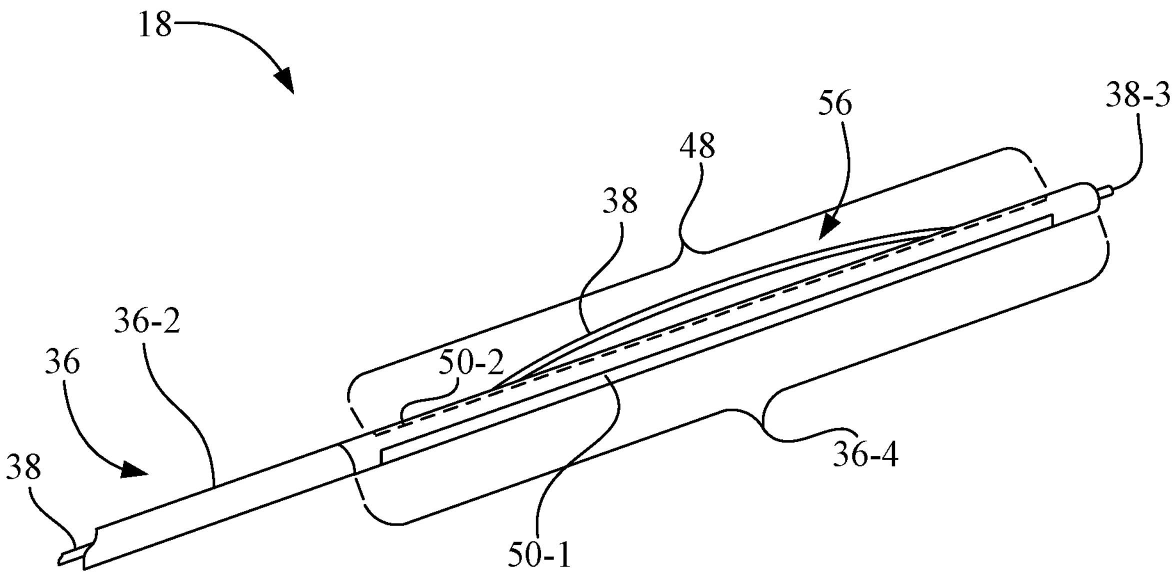
FIG. 5 is another perspective view of the arrangement of FIG. 4 that shows the bend portion of the elongate corewire radially extending through a second elongate slot of the sheath of the atherectomy catheter.

Referring also to FIGS. 4 and 5, each of elongate slot 50-1 and elongate slot 50-2 of side wall 36-5 of sheath 36 is configured, e.g., in size and shape, to receive a bend portion 56 of proximal wire portion 38-2, i.e., proximal to outer bulge portion 52, of elongate corewire 38. Bend portion 56 of proximal wire portion 38-2 of elongate corewire 38 may be created, for example, by retracting sheath 36 with a retraction operation of retraction-extension mechanism 40, wherein distal interior protrusion 42-2 of entrapment boundary region 42 of side wall 36-5 is pulled against the distal end of outer bulge portion 52 of elongate corewire 38 as the length of sheath 36 is shortened relative to the length of elongate corewire 38, so as to buckle elongate corewire 38.

With reference to FIGS. 1-5, when atherectomy catheter 18 is to be operated and energized in a radial ablation (atherectomy) mode, the bend portion 56 of proximal wire portion 38-2 of elongate corewire 38 may be caused to radially extend through at least one of elongate slot 50-1 and elongate slot 50-2, outwardly beyond outer surface 36-9 of side wall 36-5, such that bend portion 56 of proximal wire portion 38-2 of elongate corewire 38 is positioned outside side wall 36-5 of sheath 36 so as to engage the circumference of the lesion that forms an occlusion in the blood vessel. Also, when bend portion 56 of elongate corewire 38 is exposed from one of elongate slot 50-1 and elongate slot 50-2 of sheath 36, handpiece 16 may be rotated by the user to in turn rotate sheath 36 and bend portion 56 of elongate corewire 38 so as to ablate the circumference of the lesion in the blood vessel as handpiece 16 is rotated.

The following items also relate to the invention:

In one embodiment, the invention relates to an atherectomy catheter that includes a sheath and an elongate corewire. The sheath may have a side wall configured to define a lumen. The sheath may have a distal sheath portion and a distal end. The side wall may be configured to define in the lumen an entrapment boundary region in the distal sheath portion. The entrapment boundary region may have a drilling allowance region. The elongate corewire may have a proximal wire portion and a distal wire portion. The distal wire portion may have an outer bulge portion and an elongate drill tip portion. The outer bulge portion is proximal to the elongate drill tip portion. The elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath.

In accordance with any of the embodiments, the entrapment boundary region may have a proximal interior protrusion and a distal interior protrusion. The proximal interior protrusion and the distal interior protrusion may be axially spaced apart along the longitudinal axis to define the drilling allowance region between the proximal interior protrusion and the distal interior protrusion. The outer bulge portion of the elongate corewire may be slidably disposed between the proximal interior protrusion and the distal interior protrusion of the sheath.

In accordance with the embodiment discussed above, the proximal interior protrusion of the sheath may be a proximal interior annular member and/or the distal interior protrusion of the sheath may be a distal interior annular member.

In accordance with any of the embodiments, the outer bulge portion may be an outer annular member.

In accordance with any of the embodiments, the drilling allowance region of the sheath of the atherectomy catheter may have a longitudinal extent and the outer bulge portion of the elongate corewire may have a longitudinal width, wherein the longitudinal extent of the drilling allowance region of the sheath is greater than the longitudinal width of the outer bulge portion of the elongate corewire so as to accommodate alternating proximal and distal movement of the distal wire portion of the elongate corewire.

In accordance with any of the embodiments of the atherectomy catheter, the entrapment boundary region of the sheath and the outer bulge portion of the elongate corewire are configured so as to retain the distal wire portion with the sheath if the proximal wire portion of the elongate corewire separates from the distal wire portion of the elongate corewire.

Optionally, in accordance with some embodiments, the side wall of the sheath of the atherectomy catheter may include a slotted region proximal to the entrapment boundary region, the slotted region may have an elongate slot that radially extends through the side wall of the sheath to the lumen, the elongate slot configured to receive a bend portion of the proximal wire portion of the elongate corewire.

In accordance with an embodiment having the slotted region, the atherectomy catheter may be configured such that when the atherectomy catheter is operated in a radial ablation mode, the bend portion of the proximal wire portion of the elongate corewire radially extends through the elongate slot beyond an outer surface of the side wall.

Optionally, in accordance with some embodiments, the atherectomy catheter may further include at least one elongate fluid passage formed in the side wall of the sheath, wherein each elongate fluid passage may have a proximal fluid port and a distal fluid port, the distal fluid port being located at the distal end of the sheath, wherein each elongate fluid passage longitudinally extends along the entrapment boundary region and is suitable to provide cooling to the distal wire portion of the elongate corewire.

In accordance with any of the embodiments, the sheath of the atherectomy catheter may be formed from a flexible biocompatible polymer, and the elongate corewire may be formed from a biocompatible metal.

In another embodiment, the invention relates to an atherectomy system that includes an ultrasonic energy source and an atherectomy catheter. The ultrasonic energy source may be configured to operate in a drilling mode and a radial ablation mode. The atherectomy catheter is coupled, or configured for coupling, to the ultrasonic energy source. The ultrasonic energy source may be configured to effect a longitudinal motion of the atherectomy catheter in the drilling mode and to effect both longitudinal motion and transverse motion of the atherectomy catheter in the radial ablation mode. The atherectomy catheter includes a sheath and an elongate corewire. The sheath may have a side wall configured to define a lumen. The sheath may have a distal sheath portion and a distal end. The side wall may be configured to define in the lumen an entrapment boundary region in the distal sheath portion. The entrapment boundary region may have a drilling allowance region. An elongate corewire may have a proximal wire portion and a distal wire portion. The distal wire portion may have an outer bulge portion and an elongate drill tip portion. The outer bulge portion is proximal to the elongate drill tip portion. The elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath.

In accordance with any of the embodiments, the entrapment boundary region may have a proximal interior protrusion and a distal interior protrusion. The proximal interior protrusion and the distal interior protrusion may be axially spaced apart along the longitudinal axis to define the drilling allowance region between the proximal interior protrusion and the distal interior protrusion. The outer bulge portion of the elongate corewire may be slidably disposed between the proximal interior protrusion and the distal interior protrusion of the sheath.

In accordance with the embodiment discussed above, the proximal interior protrusion of the sheath may be a proximal interior annular member and/or the distal interior protrusion of the sheath may be a distal interior annular member.

In accordance with any of the embodiments, the outer bulge portion may be an outer annular member.

In accordance with any of the embodiments, the drilling allowance region of the sheath of the atherectomy catheter and system may have a longitudinal extent and the outer bulge portion of the elongate corewire may have a longitudinal width, wherein the longitudinal extent of the drilling allowance region of the sheath is greater than the longitudinal width of the outer bulge portion of the elongate corewire so as to accommodate alternating proximal and distal movement of the distal wire portion of the elongate corewire.

In accordance with any of the embodiments of the atherectomy catheter and system, the entrapment boundary region of the sheath and the outer bulge portion of the elongate corewire are configured so as to retain the distal wire portion with the sheath if the proximal wire portion of the elongate corewire separates from the distal wire portion of the elongate corewire.

Optionally, in accordance with some embodiments, the side wall of the sheath of the atherectomy catheter and system may include a slotted region proximal to the entrapment boundary region, the slotted region may have an elongate slot that radially extends through the side wall of the sheath to the lumen, the elongate slot configured to receive a bend portion of the proximal wire portion of the elongate corewire.

In accordance with an embodiment having the slotted region, the atherectomy catheter and system may be configured such that when the atherectomy system is operated in the radial ablation mode, the bend portion of the proximal wire portion of the elongate corewire radially extends through the elongate slot beyond an outer surface of the side wall.

Optionally, in accordance with some embodiments, the atherectomy system may further include a fluid source configured to supply a cooling fluid, and the atherectomy catheter may further include at least one elongate fluid passage formed in the side wall of the sheath, the at least one elongate fluid passage coupled in fluid communication with the fluid source, and wherein each elongate fluid passage may have a proximal fluid port and a distal fluid port, the distal fluid port being located at the distal end of the sheath, wherein each elongate fluid passage longitudinally extends along the entrapment boundary region and is suitable for carrying the cooling fluid supplied by the fluid source to cool the distal wire portion of the elongate corewire.

In accordance with any of the embodiments, the sheath of the atherectomy catheter of the atherectomy system may be formed from a flexible biocompatible polymer, and the elongate corewire may be formed from a biocompatible metal.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An atherectomy catheter, comprising:

a sheath having a side wall configured to define a lumen, the sheath having a distal sheath portion and a distal end, the side wall configured to define in the lumen an entrapment boundary region in the distal sheath portion, the entrapment boundary region having a drilling allowance region; and an elongate corewire having a proximal wire portion and a distal wire portion, the distal wire portion having an outer bulge portion and an elongate drill tip portion, the outer bulge portion being proximal to the elongate drill tip portion; and wherein the elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath; and wherein the entrapment boundary region has a proximal interior protrusion and a distal interior protrusion, the proximal interior protrusion and the distal interior protrusion being axially spaced apart along the longitudinal axis to define the drilling allowance region between the proximal interior protrusion and the distal interior protrusion, the proximal interior protrusion and the distal interior protrusion each define an inner diameter that is less than an inner diameter of the drilling allowance region, and wherein the outer bulge portion of the elongate corewire is slidably disposed between the proximal interior protrusion and the distal interior protrusion of the sheath, the proximal interior protrusion and the distal interior protrusion limiting movement of the outer bulge portion along the longitudinal axis.

2. The atherectomy catheter according to claim 1, wherein the proximal interior protrusion of the sheath is a proximal interior annular member and/or the distal interior protrusion of the sheath is a distal interior annular member.

3. The atherectomy catheter according to claim 1, wherein the outer bulge portion is an outer annular member.

4. The atherectomy catheter according to claim 1, wherein the drilling allowance region of the sheath has a longitudinal extent and the outer bulge portion of the elongate corewire has a longitudinal width, wherein the longitudinal extent of the drilling allowance region of the sheath is greater than the longitudinal width of the outer bulge portion of the elongate corewire so as to accommodate alternating proximal and distal movement of the distal wire portion of the elongate corewire.

5. The atherectomy catheter according to claim 1, wherein the entrapment boundary region of the sheath and the outer bulge portion of the elongate corewire are configured so as to retain the distal wire portion with the sheath if the proximal wire portion of the elongate corewire separates from the distal wire portion of the elongate corewire.

6. The atherectomy catheter according to claim 1, wherein the side wall of the sheath includes a slotted region proximal to the entrapment boundary region, the slotted region having an elongate slot that radially extends through the side wall of the sheath to the lumen, the elongate slot configured to receive a bend portion of the proximal wire portion of the elongate corewire.

7. The atherectomy catheter according to claim 6, configured such that when the atherectomy catheter is operated in a radial ablation mode, the bend portion of the proximal wire portion of the elongate corewire radially extends through the elongate slot beyond an outer surface of the side wall.

8. The atherectomy catheter according to claim 1, further comprising at least one elongate fluid passage formed in the side wall of the sheath, wherein the at least one elongate fluid passage has a proximal fluid port and a distal fluid port, the distal fluid port being located at the distal end of the sheath, and wherein the at least one elongate fluid passage longitudinally extends along the entrapment boundary region and is suitable to provide cooling to the distal wire portion of the elongate corewire.

9. The atherectomy catheter according to claim 1, wherein the sheath is formed from a flexible biocompatible polymer, and the elongate corewire is formed from a biocompatible metal.

10. An atherectomy system, comprising:

an ultrasonic energy source configured to operate in a drilling mode and a radial ablation mode; and an atherectomy catheter coupled, or configured for coupling, to the ultrasonic energy source, the ultrasonic energy source configured to effect a longitudinal motion of the atherectomy catheter in the drilling mode and to effect both longitudinal motion and transverse motion of the atherectomy catheter in the radial ablation mode, the atherectomy catheter comprising:

a sheath having a side wall configured to define a lumen, the sheath having a distal sheath portion and a distal end, the side wall configured to define in the lumen an entrapment boundary region in the distal sheath portion, the entrapment boundary region having a drilling allowance region; and an elongate corewire having a proximal wire portion and a distal wire portion, the distal wire portion having an outer bulge portion and an elongate drill tip portion, the outer bulge portion being proximal to the elongate drill tip portion; and wherein the elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath; and wherein the entrapment boundary region has a proximal interior protrusion and a distal interior protrusion, the proximal interior protrusion and the distal interior protrusion being axially spaced apart along the longitudinal axis to define the drilling allowance region between the proximal interior protrusion and the distal interior protrusion, the proximal interior protrusion and the distal interior protrusion each define an inner diameter that is less than an inner diameter of the drilling allowance region, and wherein the outer bulge portion of the elongate corewire is slidably disposed between the proximal interior protrusion and the distal interior protrusion of the sheath, the proximal interior protrusion and the distal interior protrusion limiting movement of the outer bulge portion along the longitudinal axis.

11. The atherectomy system according to claim 10, wherein the proximal interior protrusion of the sheath is a proximal interior annular member and/or the distal interior protrusion of the sheath is a distal interior annular member.

12. The atherectomy system according to claim 10, wherein the outer bulge portion is an outer annular member.

13. The atherectomy system according to claim 10, wherein the drilling allowance region of the sheath has a longitudinal extent and the outer bulge portion of the elongate corewire has a longitudinal width, wherein the longitudinal extent of the drilling allowance region of the sheath is greater than the longitudinal width of the outer bulge portion of the elongate corewire so as to accommodate alternating proximal and distal movement of the distal wire portion of the elongate corewire.

14. The atherectomy system according to claim 10, wherein the entrapment boundary region of the sheath and the outer bulge portion of the elongate corewire are configured so as to retain the distal wire portion with the sheath if the proximal wire portion of the elongate corewire separates from the distal wire portion of the elongate corewire.

15. The atherectomy system according to claim 11, wherein the side wall of the sheath includes a slotted region proximal to the entrapment boundary region, the slotted region having an elongate slot that radially extends through the side wall of the sheath to the lumen, the elongate slot configured to receive a bend portion of the proximal wire portion of the elongate corewire.

16. The atherectomy system according to claim 15, configured such that when the atherectomy system is operated in the radial ablation mode, the bend portion of the proximal wire portion of the elongate corewire radially extends through the elongate slot beyond an outer surface of the side wall.

17. The atherectomy system according to claim 10, further comprising:

a fluid source configured to supply a cooling fluid; and at least one elongate fluid passage formed in the side wall of the sheath, the at least one elongate fluid passage coupled in fluid communication with the fluid source, and wherein each elongate fluid passage has a proximal fluid port and a distal fluid port, the distal fluid port being located at the distal end of the sheath, wherein each elongate fluid passage longitudinally extends along the entrapment boundary region and is suitable for carrying the cooling fluid supplied by the fluid source to cool the distal wire portion of the elongate corewire.

18. The atherectomy system according to claim 10, wherein the sheath is formed from a flexible biocompatible polymer, and the elongate corewire is formed from a biocompatible metal.

19. An atherectomy catheter, comprising:

a sheath having a side wall configured to define a lumen, the sheath having a distal sheath portion and a distal end, the side wall configured to define in the lumen an entrapment boundary region in the distal sheath portion, the entrapment boundary region having a drilling allowance region; and an elongate corewire having a proximal wire portion and a distal wire portion, the distal wire portion having an outer bulge portion and an elongate drill tip portion, the outer bulge portion being proximal to the elongate drill tip portion; and wherein the elongate corewire is located in the lumen of the sheath with the outer bulge portion of the elongate corewire slidably disposed in the drilling allowance region of the sheath, and with the elongate drill tip portion of the elongate corewire distally protruding from the distal end of the sheath; and wherein the side wall of the sheath includes a slotted region proximal to the entrapment boundary region, the slotted region having an elongate slot that radially extends through the side wall of the sheath to the lumen, the elongate slot configured to receive a bend portion of the proximal wire portion of the elongate corewire.

20. The atherectomy catheter according to claim 19, configured such that when the atherectomy catheter is operated in a radial ablation mode, the bend portion of the proximal wire portion of the elongate corewire radially extends through the elongate slot beyond an outer surface of the side wall.

* * * * *